United States Patent [19]

Hemmerle et al.

[11] Patent Number: 5,451,573
[45] Date of Patent: Sep. 19, 1995

[54] SUBSTITUTED CYCLOHEXANE DERIVATIVES FOR THE TREATMENT OF DISEASES

[75] Inventors: Horst Hemmerle, Lorsch; Peter Schindler, Bad Soden; Roland Utz, Messel; Robert Rippel, Hofheim; Andreas Herling, Bad Camberg, all of Germany

[73] Assignee: Hoechst Aktiengesellschaft, Frankfurt am Main, Germany

[21] Appl. No.: 116,564

[22] Filed: Sep. 7, 1993

[30] Foreign Application Priority Data

Sep. 9, 1992 [DE] Germany .................. 42 30 156.4

[51] Int. Cl.$^6$ ................ A61K 31/675; A61K 31/415; A61K 31/38; A61K 31/435

[52] U.S. Cl. ..................................... 514/89; 514/95; 514/99; 514/143; 514/148; 514/277; 514/357; 514/399; 514/438; 514/445; 514/519; 514/506; 514/866; 560/19; 560/20; 560/61; 560/62; 560/63; 560/76; 560/104; 549/66; 549/79; 548/335.5; 548/341.5; 558/60; 558/170; 558/178; 558/179

[58] Field of Search .............. 560/61, 19, 20, 62, 560/63, 76, 104; 514/866, 89, 95, 99, 143, 148, 277, 357, 438, 445, 519, 399, 506; 548/335.5, 341.5; 549/79, 66; 558/60, 170, 178, 179

[56] References Cited

FOREIGN PATENT DOCUMENTS

0163270A2 12/1985 European Pat. Off. .
WO87/04619 8/1987 WIPO .

OTHER PUBLICATIONS

S. E. Kahn et al., "The Pathophysiology of Type II (Noninsulin-Dependent) Diabetes Mellitus: Implications for Treatment," Diabetes Mellitus—Theory and Practice, 4TH Ed., Elsevier, N.Y., Chapter 26, pp. 436–456 (1990).
S. Efendic et al., "Mild Type II Diabetes Markedly Increases Glucose Cycling in the Postabsorptive State and during Glucose Infusion Irrespective of Obesity," J. Clin. Invest. 81, pp. 1953–1961 (Jun. 1988).
S. Ashcroft et al., "Effects of Phloretin and Dextran-Linked Phloretin On Pancreatic Islet Metabolism and Insulin Release," Biochimca Et Biophysica Acta, 538, pp. 334–342 (1978).
P. List et al., "Hagers Handbuch der Pharmazeutischen Praxis," 4. Ausgabe, Band 4, pp. 200–210; 415–418 (1973).
V. Litvinenko et al., "Gerbstoffe Und Oxyzimtsäureabkömmlinge in Labiaten," Planta Medica, Band 27, pp. 372–380 (1975).
S. Juchi et al., "Anti–allergic foods containing caffeic and/or caffetannie acid," Chemical Abstracts, Band 104, Nr. 17, 28, p. 573 (1986).
H. Taguchi et al., "Pharmaceuticals for treatment of influenza virus infection," Chemical Abstracts, Band 104, Nr. 14, 7, p. 402 (1986).
"Chlorogensäure in Semen Coffeae und ihre Veränderung beim Röstprozeβ*", R. Krasemann, Archiv Der Pharmazie 293/65(8):721–733 (1960).
"Isolation And Structural Elucidation Of A New Lipoxygenase Inhibitor From Gardeniae Fructus", Nishizawa et al., Chem. Pharm. Bull. 34(3):1419–1421 (1986).

*Primary Examiner*—C. Warren Ivy
*Assistant Examiner*—Amelia Owens
*Attorney, Agent, or Firm*—Finnegan, Henderson, Farabow, Garrett & Dunner

[57] ABSTRACT

Substituted cyclohexane derivatives for the treatment of diseases Esters of cyclohexane derivatives of the formula I

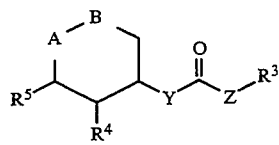

in which A—B, $R^3$, $R^4$, $R^5$, Y and Z have the meanings indicated, for use as inhibitors of the glucose-6-phosphatase system of the liver in mammals are described. The compounds are suitable for the production of pharmaceutical preparations.

13 Claims, No Drawings

SUBSTITUTED CYCLOHEXANE DERIVATIVES FOR THE TREATMENT OF DISEASES

The clinical picture of diabetes is characterized by increased blood sugar values. In insulin-dependent or type I diabetes, the cause is the death of the insulin-producing β-cells of the pancreas; treatment is therefore carried out by insulin administration (substitution therapy). The non-insulin-dependent or type II diabetes, on the other hand, is characterized by a reduced insulin action on muscle tissue and fatty tissue (insulin resistance) and an increased glucose production of the liver. The causes of these metabolic disorders are still largely unexplained. The established therapy with sulfonylureas attempts to compensate for the insulin resistance by increasing the endogenous release of insulin, but does not lead in all cases to a normalization of the blood sugar level and may not check the progress of the disease; many type II diabetics finally become insulin-dependent due to "exhaustion" of the β-cells and suffer from late damage such as cataracts, nephropathies and angiopathies.

Novel therapy principles for the treatment of type II diabetes are therefore desirable.

The concentration of the blood glucose in the fasting state is determined by the glucose production of the liver. It was possible for various teams to show that the increase in the blood sugar values in type II diabetes correlates with a proportionally increased release of glucose from the liver. The glucose released into the blood from the liver can be formed both by degradation of liver glycogen (glycogenolysis) and by gluconeogenesis.

Glucose-6-phosphate is the common end product both of gluconeogenesis and of glycogenolysis. The terminal step of the hepatic release of glucose from glucose-6-phosphate is catalyzed by glucose-6-phosphatase (EC 3.1.3.9). Glucose-6-phosphatase is a multienzyme complex occurring in the endoplasmic reticulum (ER). This enzyme complex consists of a glucose-6-phosphate translocase present in the ER membrane, a glucose-6-phosphatase localized on the luminal side of the endoplasmic reticulum and of a phosphate translocase [for a general survey see: Ashmore, J. and Weber G., "The Role of Hepatic Glucose-6-phosphatase in the Regulation of Carbohydrate Metabolism", in Vitamins and Hormones, Vol. XVII (Harris R. S., Marrian G. F., Thimann K. V., eds), 92–132, (1959); Burchell A., Waddell I. D., "The molecular basis of the hepatic microsomal glucose-6-phosphatase system", Biochim. Biophys. Acta 1092, 129–137, (1990)]. The extensive literature available shows that under all conditions investigated which lead to increased blood glucose values in animal experiments, streptozotocin, alloxan, cortisone, thyroid hormones and fasting, the activity of this multienzyme complex is also increased. Moreover, numerous investigations indicate that the elevated glucose production observed in type II diabetics is associated with an elevated glucose-6-phosphatase activity. The importance of the glucose-6-phosphatase system for a normal glucose homeostasis is further underlined by the hypoglycemic symptoms of patients with glycogenosis type Ib, who lack the translocase component of the glucose-6-phosphate system.

A reduction of the glucose-6-phosphatase activity by suitable active substances (inhibitors) should lead to a correspondingly reduced hepatic glucose release. These active substances should be able to adjust the glucose production of the liver to the effective peripheral consumption. The blood glucose values which, as a result, are reduced in the fasting state of type II diabetics, may moreover have also had a preventive action with respect to diabetic late damage.

A number of non-specific inhibitors of glucose-6-phosphatase have been described in the literature, such as phlorhizin [Soodsma, J. F., Legler, B. and Nordlie, R. C., J. Biol. Chem. 242, 1955–1960, (1967)], 5,5'-dithiobis-2-nitrobenzoic acid [Wallin, B. K. and Arion, W. J., Biochem. Biophys. Res. Commun. 48, 694–699, (1972)], 2,2'-diisothiocyanatostilbene and 2-isothiocyanato-2'-acetoxystilbene [Zoccoli, M. A. and Karnowski, M. L., J. Biol. Chem. 255, 1113–1119, (1980)]. To date, however, there are still no therapeutically utilizable inhibitors of the glucose-6-phosphatase system available.

Substituted cyclohexane derivatives, which are defined in greater detail below, are compounds from the chemical and biological literature which are known in some cases and which could be isolated from numerous plants (R. Krasemann, Arch. Pharm. 293, 721 (1960)). However, only little is known about the pharmacological and biochemical actions of these esters. Chlorogenic acid, a typical representative of the compounds mentioned here, has been described, inter alia, as an inhibitor of lipoxygenase (M. Nishizawa et al., Chem. Pharm. Bull., 34(3), 1419 (1986)).

We have now found that certain esters of substituted cyclohexanecarboxylic acids, such as e.g. chlorogenic acid (No. 17 of the compounds investigated by us), are inhibitors of the glucose-6-phosphatase system.

The invention therefore relates to esters of cyclohexane derivatives, of the formula I

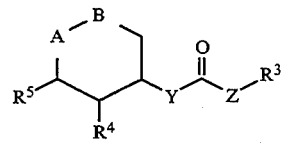

in which
A—B is the group

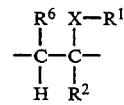

or
the group

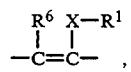

$R^1$ is: CN, COOH, COO—($C_1$–$C_4$-alkyl), $C_1$–$C_4$-alkanoyl, $SO_3$—($C_1$–$C_4$-alkyl), $SO_3H$, PO(OH)$_2$, PO(OH)(O—$C_1$–$C_4$-alkyl) or PO(O—$C_1$–$C_4$-alkyl)$_2$, $R^2$ is: H, OH or F, $R^3$ is: H, phenyl, naphthyl, pyridyl, thienyl or furyl, where the aromatic or heteroaromatic system can be monosubstituted or polysubstituted by F, Cl, Br, I, OH, $NO_2$, $C_1$–$C_4$-alkanoyl, $C_1$–$C_4$-alkoxy, $C_1$–$C_4$-alkyl, phenyl, phenoxy, thienyl, furyl, pyridyl, imidazolyl or benzyloxy, where the substituents are identical or different, $R^4$, $R^5$ and $R^6$ are: H, OH, F, Cl, Br, $C_1$-$C_4$-alkanoyl, $C_1$-$C_4$-alkyl, phenyl, phenoxy, thienyl, furyl, pyridyl, imidazolyl or benzyloxy, where $R^4$, $R^5$ and $R^6$ are identical or different, X is: —$(CH_2)_n$—, —CH=CH— or —$CH_2OCH_2$—,
Y is: —$(CH_2)_n$—,O, S or NH,
Z is: —$(CH_2)_n$— or —CH=CH— and
n is: zero, 1, 2, 3 or 4 for use as inhibitors of the glucose-6-phosphatase system of the liver in mammals.

The use of those compounds of the formula I is preferred in which the radicals have the following meaning:

$R^1$ is: COOH, COO—($C_1$-$C_4$-alkyl), PO(OH)$_2$, PO(OH)(O—$C_1$-$C_4$-alkyl) or PO(O—$C_1$-$C_4$-alkyl)$_2$,
$R^2$ is: H or OH,
$R^3$ is: H, phenyl, naphthyl, pyridyl, thienyl or furyl, where the aromatic or heteroaromatic system can be monosubstituted, disubstituted or trisubstituted by F, Cl, Br, I, NO$_2$, OH, $C_1$-$C_4$-alkanoyl, $C_1$-$C_4$-alkoxy, $C_1$-$C_4$-alkyl, phenyl, phenoxy, thienyl, furyl, pyridyl, imidazolyl or benzyloxy, where the substituents are identical or different,
$R^4$, $R^5$ and $R^6$ are: H, OH, F, Cl, Br, $C_1$-$C_4$-alkanoyl, $C_1$-$C_4$-alkyl, phenyl, phenoxy, thienyl, furyl, pyridyl, imidazolyl or benzyloxy, where $R^4$, $R^5$ and $R^6$ are identical or different,
X is: —$(CH_2)_n$—, —CH=CH— or —$CH_2OCH_2$—,
Y is: —$(CH_2)_n$—, O, S or NH,
Z is: —$(CH_2)_n$— or —CH=CH— and
n is: zero, 1, 2, 3 or 4.

The use of those compounds of the formula I is particularly preferred in which the radicals have the following meaning:

$R^1$ is: COOH or COO—($C_1$-$C_4$- alkyl),
$R^2$ is: H or OH,
$R^3$ is: H, phenyl, naphthyl, pyridyl, thienyl or furyl, where the aromatic or heteroaromatic system can be monosubstituted, disubstituted or trisubstituted by identical or different F, Cl, OH, NO$_2$, $C_1$-$C_4$-alkanoyl, $C_1$-$C_4$-alkoxy, $C_1$-$C_4$-alkyl, phenyl, phenoxy or benzyloxy,
$R^4$, $R^5$ and $R^6$ are: H or OH, where $R^4$, $R^5$ and $R^6$ are identical or different,
X is: —$(CH_2)_n$— and n=zero, 1 or 2,
Y is: O or NH,
Z is: —$(CH_2)_n$—, where n=0 or 2, or —CH=CH—.

The alkyl, alkoxy and alkanoyl radicals present in the compounds of the formula I are straight-chain or branched.

The invention furthermore relates to the use of compounds of the formula I for the treatment of diseases which are associated with an increased activity of the glucose-6-phosphatase system.

The invention also relates to the use of compounds of the formula I for the treatment of diseases which are associated with an increased glucose production of the liver.

The invention additionally relates to the use of compounds of the formula I for the treatment of type II diabetes (non-insulin-dependent or adult-onset diabetes).

The invention furthermore comprises the use of compounds of the formula I for the production of medicaments for the treatment of diabetes and other disorders which are characterized by an increased discharge of glucose from the liver or an increased activity of the glucose-6-phosphatase system.

The action of the compounds according to the invention on the glucose-6-phosphatase system was investigated in an enzyme test in liver microsomes.

Fresh liver organs of male Wistar rats were used for the preparation of the microsome fraction containing the glucose-6-phosphatase and processed as described in the literature [Canfield, W. K. and Arion, W. J., J. Biol. Chem. 263, 7458-7460, (1988)]. This microsome fraction can be stored at −70° C. for at least 2 months without significant loss of activity.

The detection of the glucose-6-phosphatase activity was carried out as indicated in the literature (Arion, W. J. in Methods Enzymol. 174, Academic Press 1989, pages 58-67) by determination of the phosphate released from glucose-6-phosphate. 0.1 ml of test mixture contained glucose-6-phosphate (1 mmol/l), the test substance, 0.1 mg of microsome fraction and 100 mmol/l of HEPES buffer (4-(2-hydroxyethyl)piperazine-1-ethanesulfonic acid), pH 7.0. The reaction was started by addition of the enzyme. After 20 min had passed at room temperature, the reaction was stopped by addition of 0.2 ml of phosphate reagent. The sample was incubated at 37° C. for 30 min, and the absorption (A) of the blue color was then measured at 570 nm. The inhibitory activity of the test substance resulted by comparison with a control reaction, which contained no test substance, according to the formula $$\text{Percentage inhibition} = \frac{A_{(control)} - A_{(test\ substance)}}{A_{(control)}} \times 100$$

The inhibitory values obtained for a number of compounds of the formula I are shown by way of example in Tables 1-3. The compounds investigated are in some cases known from the literature. The preparation is described in the exemplary embodiments.

TABLE 1

| $R^3$ | Concentration [M] | Inhibition [%] | Compound No. |
|---|---|---|---|
| HO-[benzene]-OH, OH | $3.1 \times 10^{-4}$ | 50 | 1 |
| HO-[benzene]-OH | $3.1 \times 10^{-4}$ | 50 | 2 |

TABLE 1-continued

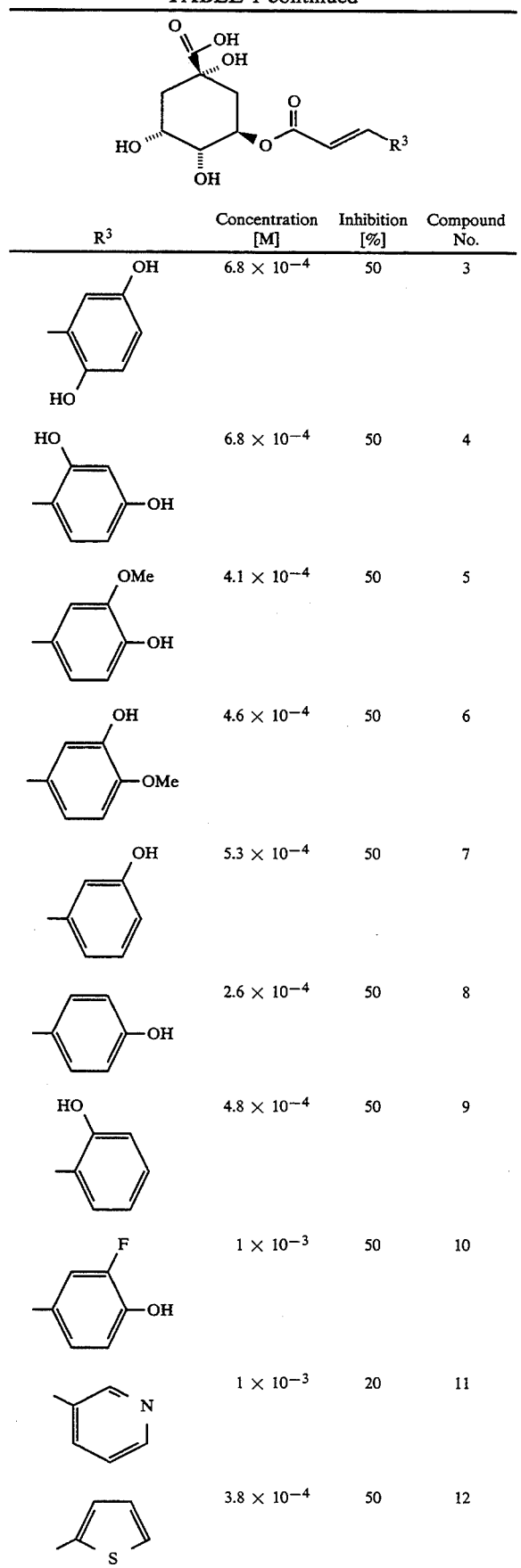

| R³ | Concentration [M] | Inhibition [%] | Compound No. |
|---|---|---|---|
| 3-methyl-1,4-dihydroxybenzene (OH, HO) | $6.8 \times 10^{-4}$ | 50 | 3 |
| 4-methyl-1,3-dihydroxybenzene (HO, OH) | $6.8 \times 10^{-4}$ | 50 | 4 |
| 3-methoxy-4-hydroxyphenyl (OMe, OH) | $4.1 \times 10^{-4}$ | 50 | 5 |
| 3-hydroxy-4-methoxyphenyl (OH, OMe) | $4.6 \times 10^{-4}$ | 50 | 6 |
| 3-hydroxyphenyl (OH) | $5.3 \times 10^{-4}$ | 50 | 7 |
| 4-hydroxyphenyl (OH) | $2.6 \times 10^{-4}$ | 50 | 8 |
| 2-hydroxyphenyl (HO) | $4.8 \times 10^{-4}$ | 50 | 9 |
| 2-fluoro-4-hydroxyphenyl (F, OH) | $1 \times 10^{-3}$ | 50 | 10 |
| 3-pyridyl (N) | $1 \times 10^{-3}$ | 20 | 11 |
| 2-thienyl (S) | $3.8 \times 10^{-4}$ | 50 | 12 |

TABLE 1-continued

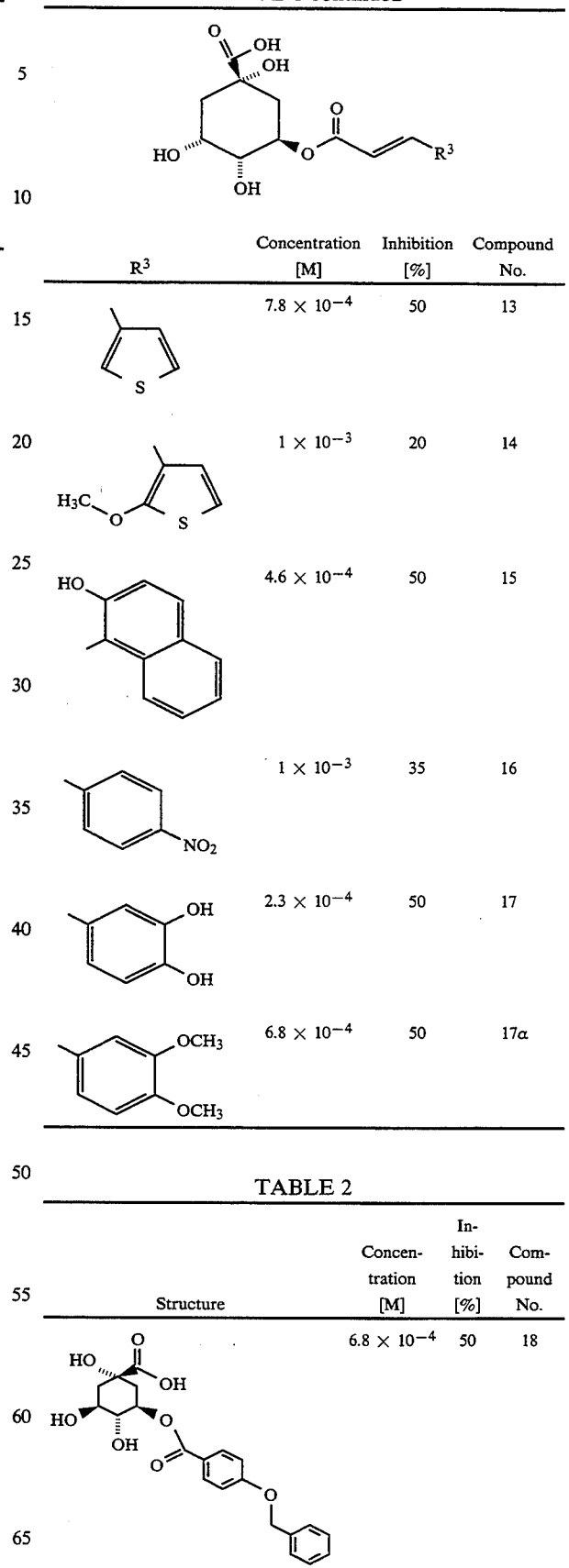

| R³ | Concentration [M] | Inhibition [%] | Compound No. |
|---|---|---|---|
| 3-methylthienyl (S) | $7.8 \times 10^{-4}$ | 50 | 13 |
| 3-methyl-2-methoxythienyl (H₃C, S) | $1 \times 10^{-3}$ | 20 | 14 |
| 2-hydroxynaphthyl (HO) | $4.6 \times 10^{-4}$ | 50 | 15 |
| 4-nitrophenyl (NO₂) | $1 \times 10^{-3}$ | 35 | 16 |
| 3,4-dihydroxyphenyl (OH, OH) | $2.3 \times 10^{-4}$ | 50 | 17 |
| 3,4-dimethoxyphenyl (OCH₃, OCH₃) | $6.8 \times 10^{-4}$ | 50 | 17a |

TABLE 2

| Structure | Concentration [M] | Inhibition [%] | Compound No. |
|---|---|---|---|
| (quinic acid 4-benzyloxybenzoate) | $6.8 \times 10^{-4}$ | 50 | 18 |

TABLE 2-continued

| Structure | Concentration [M] | Inhibition [%] | Compound No. |
|---|---|---|---|
| (structure) | $9.2 \times 10^{-4}$ | 50 | 19 |

TABLE 3

$$R = \text{(cinnamoyl-4-hydroxyphenyl group)}$$

| Structure | Concentration [M] | Inhibition [%] | Compound No. |
|---|---|---|---|
| (structure) | $1 \times 10^{-3}$ | 10 | 20a |
| (structure) | $1 \times 10^{-3}$ | 30 | 20 |
| (structure) | $2.3 \times 10^{-4}$ | 50 | 21 |
| (structure) | $1 \times 10^{-3}$ | 20 | 22 |
| (structure) | $1 \times 10^{-3}$ | 30 | 23 |

TABLE 3-continued $$R = \text{(cinnamoyl-4-hydroxyphenyl group)}$$

| Structure | Concentration [M] | Inhibition [%] | Compound No. |
|---|---|---|---|
| (structure) | $1 \times 10^{-3}$ | 45 | 24 |
| (structure) | $2.5 \times 10^{-4}$ | 50 | 25 |
| (structure) | $1 \times 10^{-3}$ | 15 | 26 |
| (structure) | $1 \times 10^{-3}$ | 15 | 27 |
| (structure) | $1 \times 10^{-3}$ | 28 | 28 |

The pharmaceuticals according to the present invention, which are prepared according to customary processes, can also contain pharmaceutically acceptable additives, such as diluents and/or excipients, in addition to compounds of the formula I. Among these are to be understood physiologically acceptable substances which, after mixing with the active compound, convert the latter into a form suitable for administration.

Oral administration is preferred

Suitable solid or liquid pharmaceutical preparation forms are, for example, tablets, coated tablets, powders, capsules, syrups, emulsions, suspensions, drops and preparations having protracted release of active compound. Frequently used excipients or diluents which may be mentioned are e.g. various sugars or types of starch, cellulose derivatives, magnesium carbonate, gelatin, animal and vegetable oils, polyethylene glycols, water or other suitable solvents and also water-containing buffering agents, which can be rendered isotonic by addition of salts. If appropriate, surface-active agents, colorants and flavorings, stabilizers, and also preservatives can additionally be used as further additives in the pharmaceutical preparations according to the invention.

Preferably, preparations can be prepared in dose units. Tablets and capsules in particular are examples of suitable dose units. Each dose unit, in particular for oral administration, can contain up to 500 mg, but preferably 10 to 200 mg, of the active constituent. However, dose units of over or under this amount can also be used, which, if appropriate, are to be divided or to be multiplied before administration. If appropriate, the dose units can be microencapsulated for oral administration in order e.g. to delay the release. Controlled release is also achieved, for example, by covering or enclosing particulate material in suitable polymers, waxes or the like.

The compounds investigated were synthesized as described below.

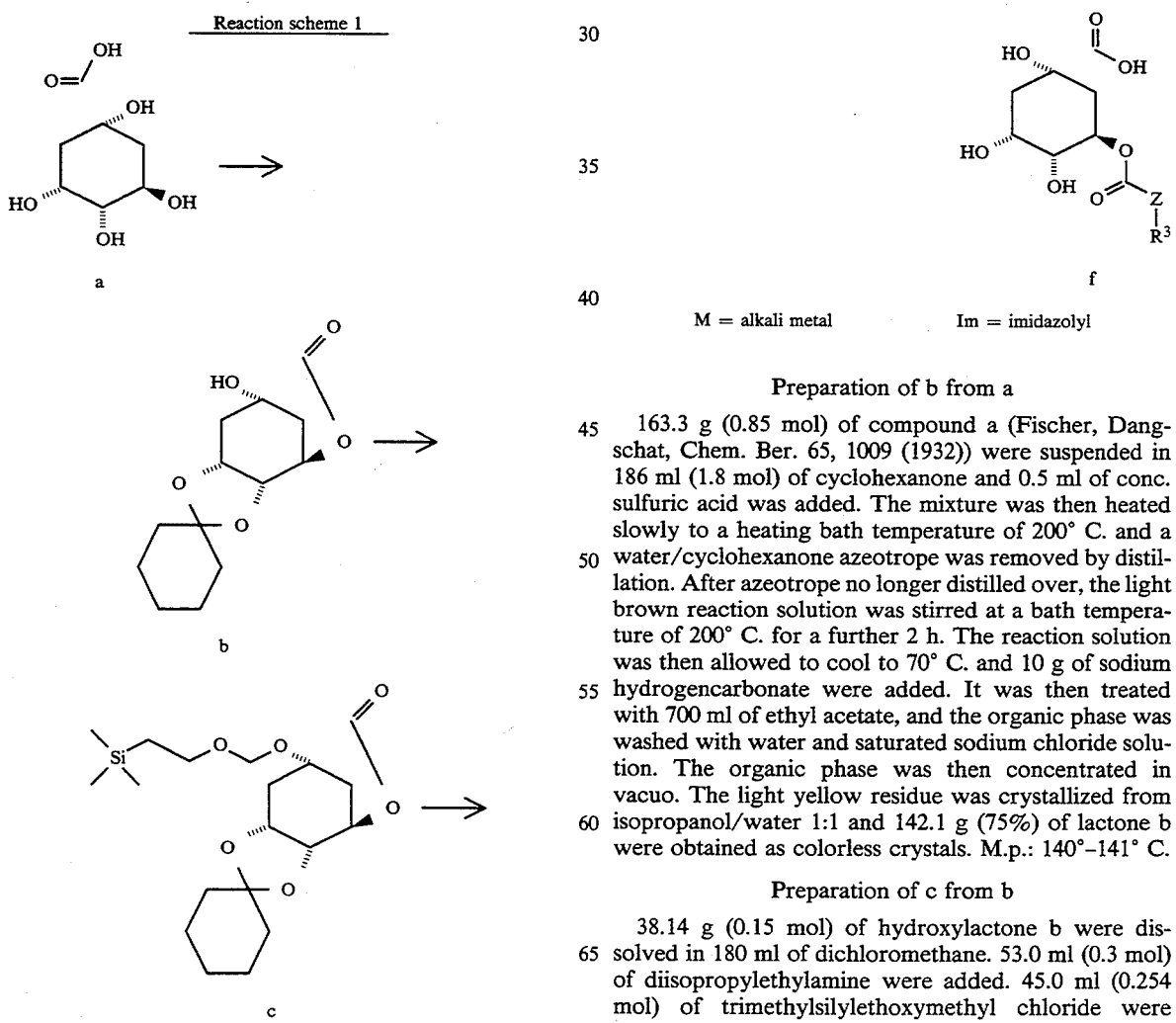

M = alkali metal    Im = imidazolyl

Preparation of b from a 163.3 g (0.85 mol) of compound a (Fischer, Dangschat, Chem. Ber. 65, 1009 (1932)) were suspended in 186 ml (1.8 mol) of cyclohexanone and 0.5 ml of conc. sulfuric acid was added. The mixture was then heated slowly to a heating bath temperature of 200° C. and a water/cyclohexanone azeotrope was removed by distillation. After azeotrope no longer distilled over, the light brown reaction solution was stirred at a bath temperature of 200° C. for a further 2 h. The reaction solution was then allowed to cool to 70° C. and 10 g of sodium hydrogencarbonate were added. It was then treated with 700 ml of ethyl acetate, and the organic phase was washed with water and saturated sodium chloride solution. The organic phase was then concentrated in vacuo. The light yellow residue was crystallized from isopropanol/water 1:1 and 142.1 g (75%) of lactone b were obtained as colorless crystals. M.p.: 140°–141° C.

Preparation of c from b 38.14 g (0.15 mol) of hydroxylactone b were dissolved in 180 ml of dichloromethane. 53.0 ml (0.3 mol) of diisopropylethylamine were added. 45.0 ml (0.254 mol) of trimethylsilylethoxymethyl chloride were added dropwise at room temperature to this solution and it was stirred at reflux temperature for 6 h. The reaction solution was then added to saturated ammonium chloride solution and extracted using ethyl acetate. The combined organic phases were extracted using cold 1N potassium hydrogensulfate solution at about 6° C. and dried using sodium sulfate. After concentration in vacuo, a light yellow residue was obtained which was crystallized from heptane/EA 6:1. 57.0 g (98%) of c were obtained. M.p.: 100°–102° C.

Preparation of d from c 1.38 g (3.6 mol) of c were dissolved in 8 ml of dioxane. After addition of 0.4 ml of water, 3.8 ml of 1N sodium hydroxide solution were added dropwise at room temperature. The reaction mixture was stirred for 2 h and then concentrated in vacuo. 1.3 g (85%) of d were obtained as an amorphous solid.

$^1$H-NMR (270 MHz, d$_6$-DMSO): d=0.01 ppm (s, 9H), 0.72–0.89 (m, 2H), 1.21–1.62 (m, 10H), 1.65–1.78 (m, 1H), 1.82–1.92 (m, 1H), 1.94–2.08 (m, 2H), 3.38–3.63 (m, 3H), 3.82–3.88 (m, 1H), 4.18–4.27 (m, 1H), 4.61–4.72 (m, 2H), 7.80–7.90 (m, 1H).

Steps d, e and f are described by example of the preparation of compound 8.

Preparation of compound 8

Reaction scheme 2:

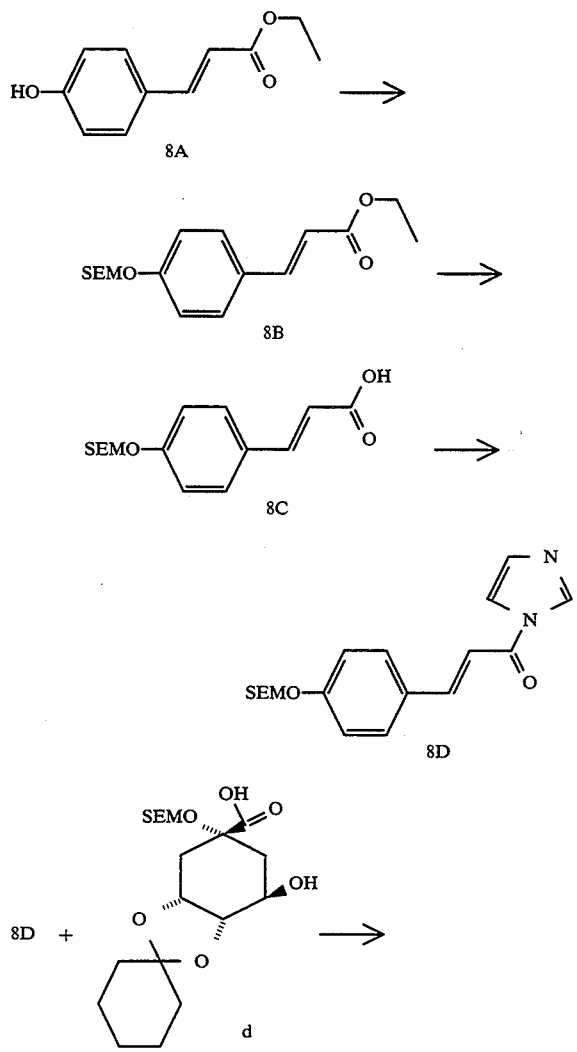

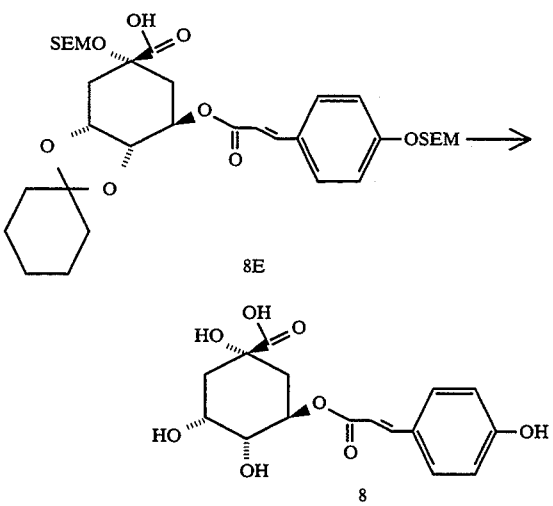

Preparation of 8C (from 8A via 8B)

10.0 g (0.052 mol) of p-hydroxycinnamic acid ester (8A) were dissolved in 60 ml of anh. dichloromethane. 27 ml (0.156 mol) of diisopropylethylamine were added and 19.5 ml (0.11 mol) of trimethylsilylethoxymethyl chloride were added dropwise at room temperature under an argon atmosphere. The mixture was stirred at room temperature for 4 h and the reaction solution was then poured onto ice-cooled ammonium chloride solution. The mixture was extracted using ethyl acetate, and the combined organic phases were washed successively with ice-cold 1N potassium hydrogensulfate solution and saturated sodium chloride solution. After drying of the organic phase using sodium sulfate, the mixture was concentrated in vacuo. 16.8 g of ether 8B were obtained, which was dissolved without further purification in 600 ml of dioxane and treated at room temperature with 160 ml (0.8 mol) of 5N sodium hydroxide solution. After 24 h, the methanol was removed by distillation in vacuo, and the aqueous suspension of the sodium salt of 8C was acidified to pH 4 using 2N hydrochloric acid. The acid 8C precipitated almost quantitatively and could be filtered off with suction and washed with water. 16.02 g of 8C were obtained. M.p.: 93°–96° C.

Preparation of 8E from 8C and d (corresponds in the general scheme 1 to stage e)

a) 7.95 g (27 mmol) of 8C were dissolved in 35 ml of anh. dimethylformamide. A solution of 4.54 g (27 mmol) of carbonyldiimidazole dissolved in 35 ml of anh. dimethylformamide was added dropwise at room temperature. This solution was then heated at 60°–70° C. for 1 h, during the course of which evolution of CO2 was to be observed.

b) 0.75 g (0.025 mol) of sodium hydride (80% strength) was added at room temperature under an argon atmosphere to a solution of 8.92 g (0.021 mol) of sodium salt d in 50 ml of anhydrous dimethylformamide. This suspension was stirred for 1 h at room temperature and the solution of the imidazolide 8D prepared as in a) was then added at 0°–5° C. The solution was stirred at 0°–5° C. for 2.5 h and the reaction mixture was then added to saturated ammonium chloride solution. The mixture was acidified to pH 4 by addition of 1N potassium hydrogensulfate solution and extracted using ethyl acetate. The combined organic phases were washed successively with saturated ammonium chloride solution, water and saturated sodium chloride solution. The organic phase was dried using sodium sulfate and concentrated in vacuo, and the oily residue was chromatographed on silica gel (eluent: ethyl acetate/n-heptane/glacial acetic acid 20:60:1). 10.3 g (78%) of 8E were obtained as a colorless oil.

¹H-NMR (270 MHz, CDCl₃): d=0.02 ppm (s, 9H), 0.05 (s, 9H), 0.91–1.03 (m, 4H), 1.5–1.78 (m, 10H), 1.91–2.05 (m, 1H), 2.28–2.42 (m, 2H), 2.57–2.63 (m, 1H), 3.68–3.90 (m, 4H), 4.14–4.20 (m, 1H), 4.42–4.52 (m, 1H), 4.91–4.96 (m, 1H), 5.11–5.18 (m, 1H), 5.24 (s, 2H), 5.21–5.34 (m, 1H), 6.32 (d, J=10 Hz, 1H), 7.02–7.08 (m, 2H), 7.42–7.5 (m, 2H), 7.65 (d, J=10 Hz, 1H), 13 (s, br, COOH), 1H).

Preparation of 8 from 8E (corresponds in the general scheme 1 to stage f)

5.02 g (7.4 mmol) of 8E were dissolved in 130 ml of dioxane and treated with 95 ml (0.19 mol) of 2N hydrochloric acid at room temperature with stirring. The mixture was stirred at room temperature for 20 h. After the reaction had ended, the clear solution was adjusted to pH 3–4 using 2N sodium hydroxide solution and concentrated in vacuo. The solid residue was stirred in ethyl acetate/methanol 3:1 and the insoluble sodium chloride was filtered off. The filtrate was concentrated again and the residue was chromatographed on silica gel (ethyl acetate/methanol/water/glacial acetic acid 100:10:10:5). 1.95 g (70%) of 8 were obtained. M.p.: 235°–238° C.

The examples (compounds) indicated in Table 4 were prepared according to the above process. The synthesis of the compounds containing hydroxy groups in the radical R³ of the general formula I differed here, by the corresponding protective group operations, from the others, in which these were not necessary.

The physical data of the examples synthesized are summarized in the following Tables 4 and 5.

TABLE 4

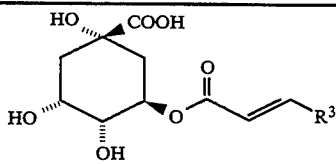

| R³ | Physical data (NMR/MS or melting point) | Compound No. |
|---|---|---|
| HO, OH, OH (trihydroxyphenyl) | m.p.: 105–110° C. | 1 |
| HO, OH (dihydroxyphenyl) | ¹H-NMR (270 MHz, d₆-DMSO): d=1.72–2.08(m, 4H), 3.51–3.62(m, 1H), 3.91–3.99(m, 1H), 4.7–4.95(m, 2H), 5.08–5.17(m, 1H), 6.49(d, J=10 Hz, 1H), 6.61–6.70(m, 1H), 6.69–6.88(m, 1H), 6.98–7.08(m, 1H), 7.82(d, J=10 Hz, 1H), 9–10(s, br, 2H), 12–13(s, br, 1H) | 2 |
| OH, HO (1,4-dihydroxyphenyl) | MS(Cl)=355.7 (M+H⁺) | 3 |
| HO, OH | m.p.: 180° C. | 4 |
| OMe, OH | m.p.: 110–120° C. | 5 |
| OH, OMe | m.p.: 166–169° C. | 6 |

TABLE 4-continued

[Structure: cyclohexane with HO, COOH at top carbon; HO, OH on other carbons; and an O-C(=O)-CH=CH-R³ ester substituent]

| R³ | Physical data (NMR/MS or melting point) | Compound No. |
|---|---|---|
| 3-hydroxyphenyl | ¹H-NMR (270 MHz, D₆-DMSO): d=1.72–2.10(m, 4H), 3.21–3.60(m, 3H), 3.90–4.00(m, 1H), 4.70–4.82(m, 1H), 4.85–4.95(m, 1H), 5.05–5.15(m, 1H), 6.37 (d, J=10 Hz, 1H), 6.81–6.85(m, 1H), 7.0–7.05(m, 1H), 7.09–7.15(m, 1H), 7.18–7.27(m, 1H), 7.5(d, J=10 Hz, 1H), 9.6(s, br, 2H), 11–13(COOH, 1H) | 7 |
| 4-hydroxyphenyl | m.p.: 235–238° C. (decomposition) | 8 |
| 2-hydroxyphenyl | m.p.: 105–110° C. | 9 |
| 3-fluoro-4-hydroxyphenyl | m.p.: 208–211° C.  MS(Cl)=357 (M+H⁺) | 10 |
| 3-pyridyl | m.p.: 195–200° C. (decomposition) | 11 |
| 2-thienyl | m.p.: 85–95° C. | 12 |
| 3-thienyl | ¹H-NMR (270 MHz, d₆-DMSO): d=1.72–2.10(m, 4H), 3.1–3.7(m, 3H), 3.90–4.00(m, 1H), 4.7–5.0(m,2H), 5.06–5.13(m, 1H), 6.32(d, J=10 Hz, 1H), 7.52–7.65(m, 3H), 7.95–8.02(m, 1H), MS(Cl) - 329.1 (M+H⁺) | 13 |
| 2-methoxy-3-methylthienyl | m.p.: 178–181° C. | 14 |
| 4-nitrophenyl | m.p.: 180–185° C. | 16 |
| 3,4-dimethoxyphenyl | ¹H-NMR (270 MHz, d₆-DMSO): d=1.73–2.10(m, 4H), 3.25–3.41(m, 1H), 3.52–3.62(m, 1H), 3.78(s, 3H), 3.82(s, 3H), 3.91–4.99(m, 1H), 4.72–4.83(m,1H), 4.86–4.92(m, 1H), 5.05–5.18(m, 1H), 6.45(d, J=10 Hz, 1H), 6.97–7.03(m, 1H), 7.18–7.27(m, 1H), 7.30–7.36(m, 1H), 7.52(d, J=10 Hz, 1H), 12.5(s, br, 2H) | 17α |

TABLE 4-continued

[Structure: quinic acid ester with cinnamoyl R³ substituent]

| R³ | Physical data (NMR/MS or melting point) | Compound No. |
|---|---|---|
| [3,4-dihydroxyphenyl] | m.p.: 208–210° C. | 17 |

TABLE 5

| Structure | Melting point | Compound No. |
|---|---|---|
| [quinic acid 2-O-(4-benzyloxybenzoyl) ester] | 165–170° C. | 18 |
| [quinic acid 2-O-(4-hydroxybenzoyl) ester] | 235–240° C. (decomposition) | 19 |

Preparation of the compound 20 or 20α

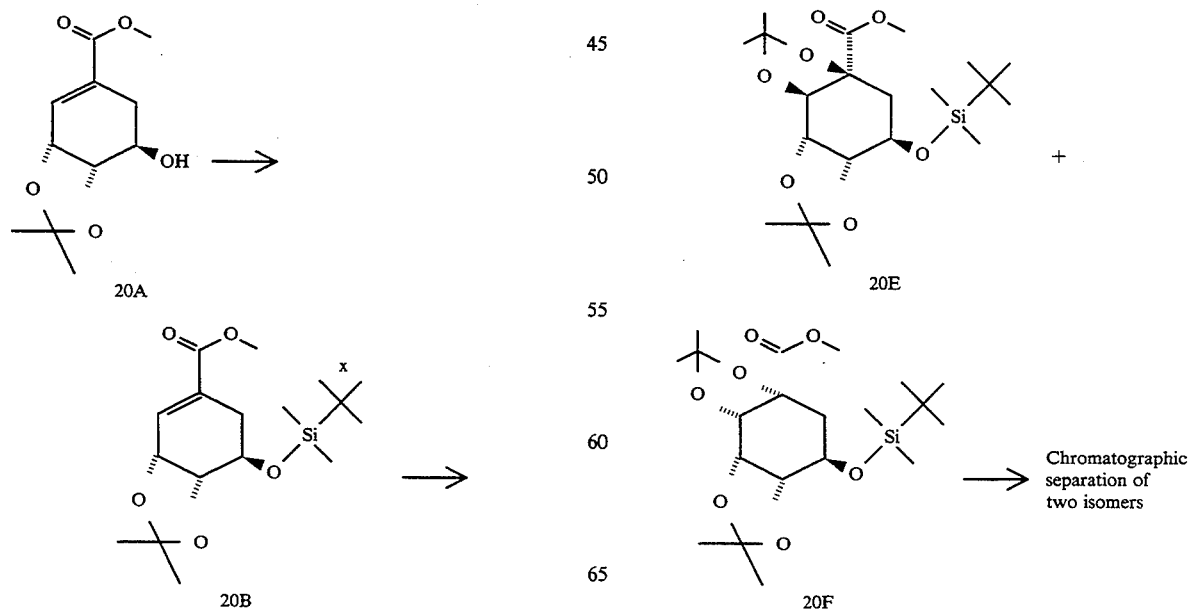

20A → 20B → 20C + 20D → 20E + 20F → Chromatographic separation of two isomers

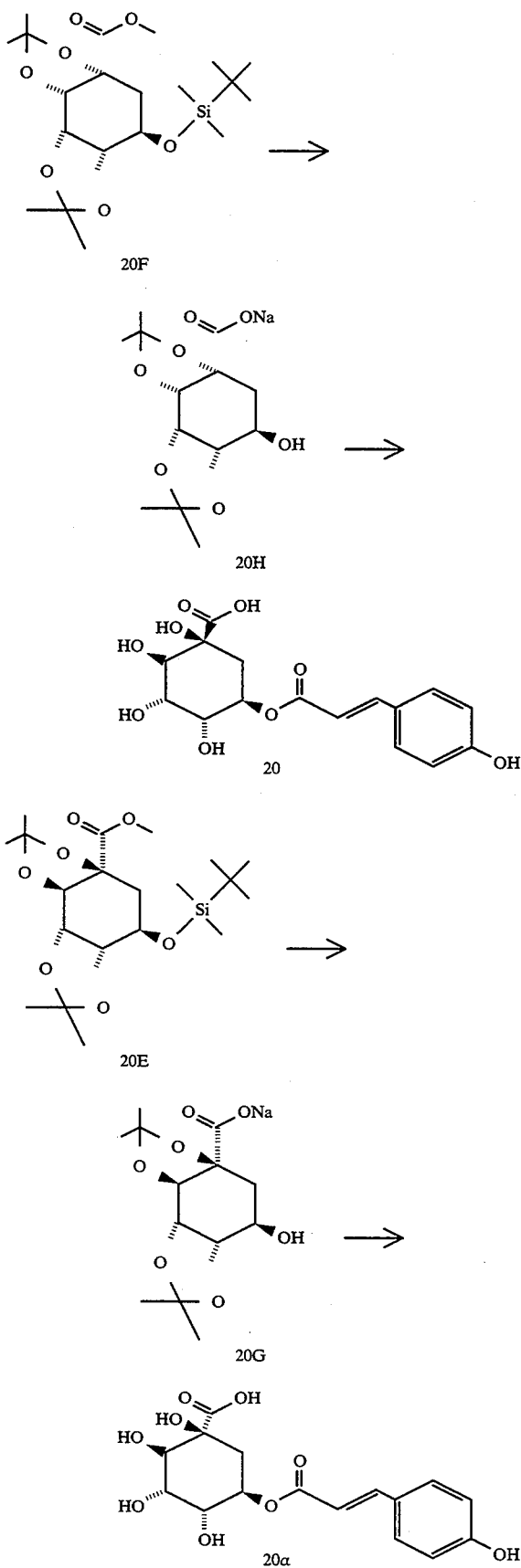

Preparation of 20B from 20A 4.0 g (17.5 mmol) of the known compound 20A (S. A. Bowles et al., Tetrahedron 46, 3981 (1990)) were dissolved in 30 ml of anhydrous dimethylformamide. 1.61 g (23.7 mmol) of imidazole and 2.64 g (12.5 mmol) of t-butyldimethylsilyl chloride were added. After 12 h at 25° C., the reaction solution was treated with 200 ml of saturated ammonium chloride solution and extracted in portions using 300 ml of methyl t-butyl ether. The combined organic phases were washed with water and saturated sodium chloride solution and dried using magnesium sulfate. 5.4 g (90%) of 20B were obtained as a colorless oil.

$^1$H-NMR (270 MHz, CDCl$_3$): δ=0.06 ppm (s, 3H), 0.09 (s, 3H), 0.76 (s, 9H), 1.39 (s, 6H), 2.23–2.40 (m, 1H), 2.48–2.62 (m, 1H) , 3.76 (s, 3H), 4.0–4.12 (m, 2H), 4.66–4.72 (m, 1H), 6.80–6.86 (m, 1H).

Preparation of 20C and 20D from 20B 5.4 g (15.8 mmol) of 20B were dissolved in 100 ml of t-butanol. 1.9 g (25.3 mmol) of trimethylamine-N-oxide and 20 ml of water were added. 100 mg (0.4 mmol) of osmium tetroxide complexed with 2.0 g of polyvinylpyridine were then added and the mixture was stirred at boiling point for 14 h. The catalyst was then filtered off, the filtrate was concentrated and the residue was chromatographed on silica gel (eluent: ethyl acetate/n-heptane 1:1). 2.5 g (42%) of 20C/20D were obtained in the ratio 3:1 as a colorless oil.

Mixture of the two isomers 20C/20D $^1$H-NMR (270 MHz, CDCl$_3$): δ=0.08–0.14 (m, 6H) , 0.88–0.92 (m, 9H), 1.38–1.40 (m, 3H), 1.51–1.55 (m, 3H), 1.80–2.0 (m, 1H), 2.28–2.48 (m, 1H), 3.61–4.52 (m,

Preparation of 20E and 20F from 20C and 20D 2.5 g (6.6 mmol) of a 3:1 mixture of 20C/20D were dissolved in 60 ml of anhydrous dichloromethane. 5 ml of 2,2-dimethoxypropane and 200 mg of pyridinium p-toluenesulfonate were added. The reaction solution was heated to boiling point for 6 h and the solution was then concentrated in vacuo. The residue, a mixture of 20E and 20F, was separated on silica gel (eluent: ethyl acetate/n-heptane 3:1) and a total of 2.4 g (87%) of 20E and 20F was obtained, in each case as colorless oils.

$^1$H-NMR (270 MHz, CDCl$_3$): δ=0.08 ppm (s, 3H), 0.09 (s, 3H), 0.90 (s, 9H), 1.34 (s, 3H), 1.39 (s, 3H), 1.45 (s, 3H), 1.50 (s, 3H), 1.72 (dd, J=13.5, J=12 Hz, 1H), 2.19 (dd, J=4.0, J=14.5 Hz, 1H), 3.81 (s, 3H), 3.81–3.92 (m, 1H), 4.05–4.11 (m, 1H), 4.42–4.48 (m, 1H), 4.68–4.70 (m, 1H).

Preparation of 20G from 20E 1.4 g (3.4 mmol) of 20E were dissolved in 30 ml of dioxane. 2 ml of 6N sodium hydroxide solution were added dropwise. After 2 h, the reaction solution was concentrated, treated with 200 ml of ethyl acetate and added to 200 ml of saturated ammonium chloride solution. This mixture was acidified to pH 5 using 1N potassium hydrogensulfate solution and the organic phase was washed with saturated sodium chloride solution and dried using sodium sulfate. After concentration, the oily residue was dissolved in 15 ml of anhydrous THF and 3.0 g (9.5 mmol) of tetrabutylammonium fluoride (trihydrate) and 0.5 ml of triethylamine were added. The solution was then heated at 60° C. for 12 h. The solution was then concentrated and the residue was purified on silica gel (eluent: ethyl acetate/n-heptane/-glacial acetic acid 30:10:1). 600 mg (54%) of 20G were obtained as a colorless oil.

Preparation of 20H from 20F 20H was obtained from 20F analogously to the preparation of 20G from 20E.

Preparation of 20 from 20H and of 20α from 20G

The synthesis of 20 and 20α was carried out analogously to the synthesis procedures d-f (as described under 8).
20:m.p.: 275° C. (decomposition)
20α: m.p.: 165°-175° C. (decomposition)

Preparation of compound 21

The lactone 21A known from the literature (S. Hanessian, Tetrahedron 45, 6623 (1989)) was converted into 21 analogously to the synthesis procedures d-f (as described under 8. M.p.: 227°-229° C.

Preparation of 22

The known compound 22A (S. Mills et al., Tetrahedron Lett. 29, 281 (1988)) was converted into 22 analogously to the synthesis procedures d-f (as described under 8). M.p.: 204°-206° C.

Preparation of 23

Reaction scheme 4

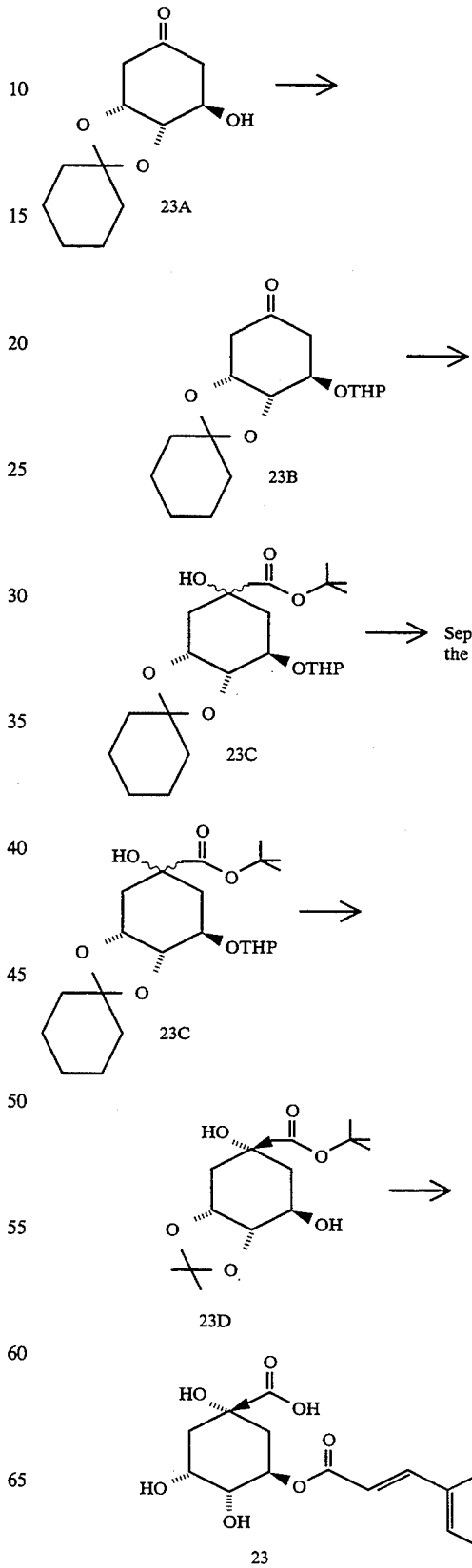

-continued
Reaction scheme 4

THP = tetrahydropyranyl

Preparation of 23B from 23A 20.0 g (88.4 mmol) of the compound 23A known from the literature (J.-C. Barriere et al., Helv. Chim. Acta 66, 296 (1983)) were dissolved in 200 ml of anhydrous dichloromethane and treated at 25° C. with 14.9 g (176.8 mmol) of dihydropyran and 200 mg of pyridinium p-toluenesulfonate. This solution was stirred at room temperature for 12 h. 500 ml of ethyl acetate were then added and the organic phase was washed with sodium hydrogencarbonate and saturated sodium chloride solution. The organic phase was dried using magnesium sulfate and concentrated in vacuo. 26.0 g (95%) of 20B were obtained as a colorless solid. M.p.: 55°–58° C.

Preparation of 23C from 23B 3.66 g (36 mmol) of diisopropylamine were dissolved in 100 ml of anhydrous tetrahydrofuran. 25 ml of 1.5 M n-butyllithium solution in hexane were added dropwise at −20° C. under argon. The reaction solution was allowed to warm to 0° C. and was then cooled again to −60° C. 4.1 g (35.3 mmol) of t-butyl acetate dissolved in 20 ml of anhydrous tetrahydrofuran were slowly added dropwise at this temperature. The solution was stirred at −60° C. for 30 minutes and 10.0 g (32.2 mmol) of 23B dissolved in 30 ml of anhydrous tetrahydrofuran were then added dropwise at −60° C. After stirring for one hour at the same temperature, the reaction mixture was hydrolyzed using saturated sodium hydrogencarbonate solution. The mixture was extracted using ethyl acetate and the combined organic phases were washed with saturated sodium chloride solution and dried using magnesium sulfate. After concentration, 11.9 g (87%) of 23C were obtained as a light brown oil.

Preparation of 23D from 23C 11.9 g (27.9 mmol) of 23C were dissolved in 200 ml of methanol. 1.8 g of pyridinium p-toluenesulfonate were added. The mixture was heated at reflux temperature for 1 h and the reaction solution was then concentrated. The residue was dissolved in 200 ml of anh. dichloromethane and 8.6 g (93.5 mmol) of dimethoxypropane were added. After 72 h at room temperature, the solution was concentrated in vacuo and the residue was purified by chromatography on silica gel (eluent: ethyl acetate/n-heptane 1:1). 6.6 g (82%) of 23D were obtained.

$^1$H-NMR (270 MHz, CDCl$_3$) d=1.35 ppm (s, 3H), 1.47 (s, 9H), 1.53 (s, 3H), 1.9–2.12 (m, 1H), 2.22–2.32 (m, 1H), 2.43 (s, 1H), 3.87–3.94 (m, 1H), 4.12–4.25 (m, 1H), 4.35–4.45 (m, 1H).

Preparation of 23 from 23D 23 was obtained as a colorless solid analogously to procedures d–f (as described under 8). M.p.: 85–92° C.

Preparation of 24

Reaction scheme 5

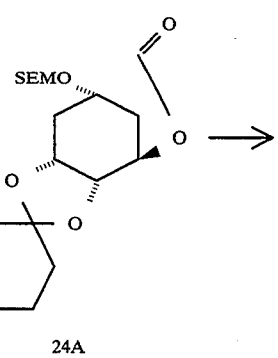

24A

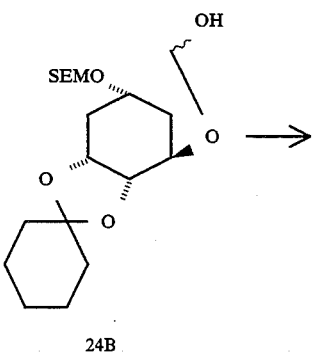

24B

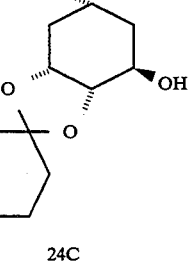

24C

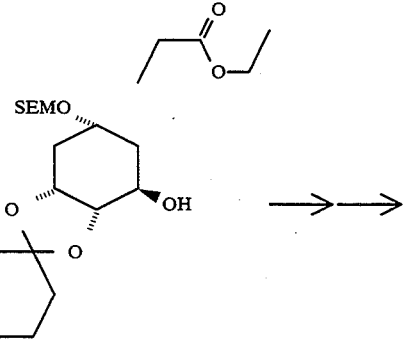

24D

-continued
Reaction scheme 5

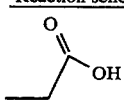
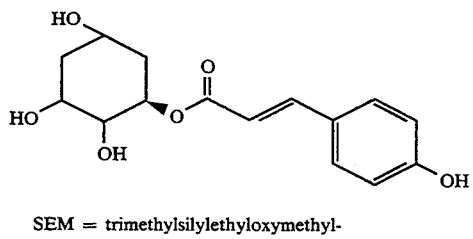

SEM = trimethylsilylethyloxymethyl-

Preparation of 24B from 24A 15.0 g (39 mmol) of 24A (J. R. Falck, J. Org. Chem., 54, 5851 (1989)) were dissolved in 200 ml of anhydrous toluene. 38 ml (43 mmol) of 1.2M diisobutylaluminum hydride solution in hexane were added dropwise at −70° C. The reaction mixture was allowed to warm to 0° C. in the course of 2 h and was hydrolyzed using 10 ml of saturated sodium hydrogencarbonate solution. 10 ml of 1N sodium hydroxide solution and 10 ml of water were then added successively. The reaction mixture was treated with 50 g of magnesium sulfate and 50 g of sodium sulfate with vigorous stirring. The mixture was stirred at room temperature for 30 min, the solid precipitate was filtered off with suction and the filtrate was concentrated. 12.9 g (85%) of 24B were obtained as a colorless oil which crystallized at 0° C. M.p.: 20°–25° C.

Preparation of 24C from 24B 7.5 g (33.5 mmol) of triethyl phosphonoacetate were added dropwise at 0° C. under an argon atmosphere to a suspension of 0.9 g (29.9 mmol) of 80% strength sodium hydride in 200 ml of anhydrous tetrahydrofuran. The reaction mixture was slowly allowed to warm to room temperature and the then clear brownish solution was cooled to −30° C. 7.7 g (19.9 mmol) of 24B dissolved in 20 ml of anhydrous tetrahydrofuran were added dropwise. This solution was stirred at −20° to 30° C. for 24 h and then treated with 100 ml of saturated ammonium chloride solution. The mixture was extracted using ethyl acetate, and the combined organic phases were washed with saturated sodium chloride solution and dried using magnesium sulfate. After concentration in vacuo, the residue was purified on silica gel (eluent: ethyl acetate/n-heptane 1:1), and 7.5 g (82%) of 24C were obtained as a colorless oil.

$^1$H-NMR (200 MHz, CDCl$_3$): δ=0.01 ppm (s, 9H), 0.85–1.0 (m, 2H), 1.1–1.85 (m, 15H), 2.1–2.25 (m, 2H), 2.35–2.5 (m, 1H), 3.42–3.9 (m, 3H), 4.1–4.4 (m, 4H), 4.65–4.8 (m, 2H), 5.92 (d, J=15 Hz, 1H). MS (FAB): 463.3 (M+Li+).

Preparation of 24D from 24C 1.0 g (2.2 mmol) of 24C were dissolved in 50 ml of ethyl acetate. 100 mg of Rh/Al$_2$O$_3$ (5% Rh) were added. The mixture was shaken at 25° C. and normal pressure under a hydrogen atmosphere for 3 h. The catalyst was filtered off and the filtrate was concentrated in vacuo. 0.95 g (94%) of 24D was obtained as a colorless solid.

Preparation of 24 from 24D 24 was obtained from 24D analogously to the synthesis procedures d–f (as described under 8). M.p.: 172° C. (H$_2$O).

Preparation of 25

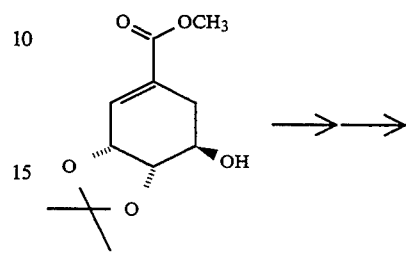

25A

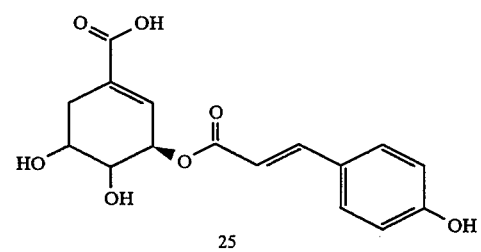

25

The compound 25 was obtained from the precursor 25A known from the literature (J. L. Pawlak et al., J. Org. Chem. 52, 1765 (1987)) analogously to the synthesis procedures d–f (as described under 8). M.p.: 75°–80° C. (foaming)

Preparation of 26 from 26A

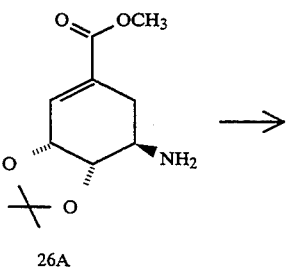

26A

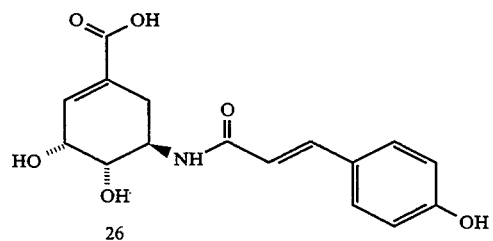

26

The compound 26 was obtained from the precursor 26A known from the literature analogously to the synthesis procedures d–f (as described under 8) as a colorless amorphous solid.

$^1$H-NMR (270 MHz, d$_6$-DMSO): d=1.95–2.14 ppm (m, 1H), 2.55–2.70 (m, 1H), 3.62–3.76 (m, 1H), 4.08–4.26 (m, 2H), 4.55–4.75 (m, 1H), 4.9–5.1 (m, 1H), 6.48 (d, J=10.0 Hz, 1H), 6.63–6.72 (m, 1H), 6.75–6.88 (m, 2H), 7.29–7.46 (m, 3H), 7.89 (d, J=5 Hz, 1H), 9.70–10.0 (1H), 12.2–12.6 (1H). MS (Cl): 225.2 (M+H⁺).

Preparation of 27 and 28

Reaction scheme 6

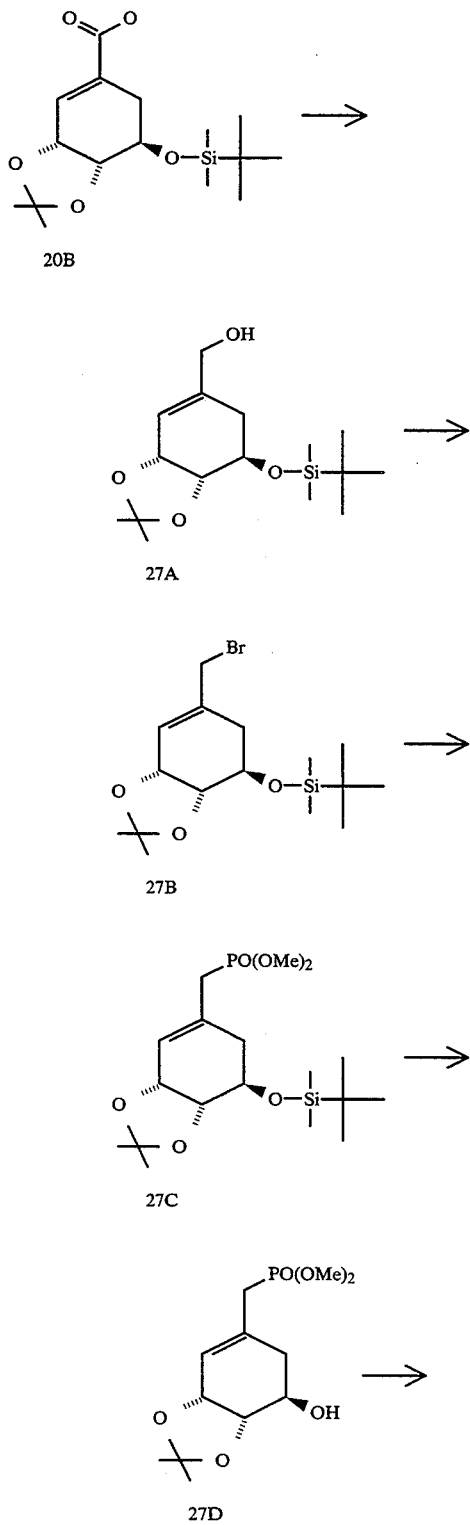

-continued
Reaction scheme 6

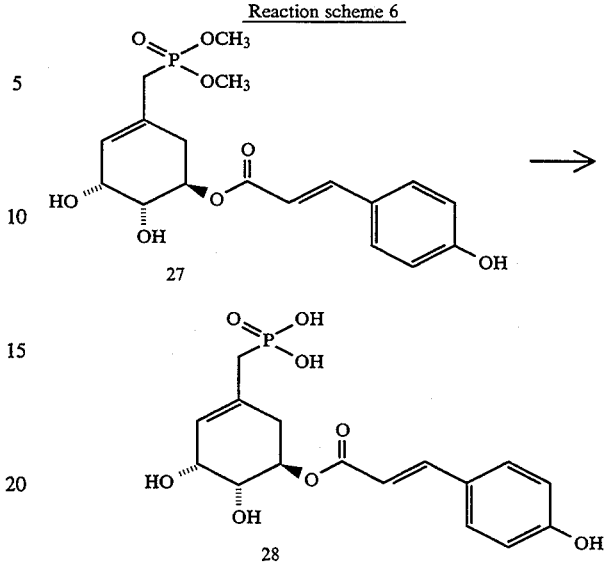

Preparation of 27A from 20B 6.0 g (17.5 mmol) of 20B were dissolved in 100 ml of anhydrous toluene. 29.2 ml of 1.2M diisobutylaluminum hydride solution in hexane were added dropwise at −20° C. The mixture was allowed to warm to 25° C. in the course of 1 h and was cooled again to 0° C., and 20 ml of a 9:1 mixture of methanol/water were cautiously added dropwise. A further 30 ml of a saturated ammonium chloride solution were then added dropwise and the reaction mixture was stirred at 25° C. for 30 min. It was then extracted using ethyl acetate and the combined organic phases were washed with saturated sodium chloride solution, dried using magnesium sulfate and concentrated in vacuo. The residue was purified by chromatography on silica gel (ethyl acetate/n-heptane 1:3). 3.5 g (63%) of 27B were obtained as a colorless oil.

¹H-NMR (270 MHz, CDCl₃): d=0.08 ppm (s, 3H), 0.11 (s, 3H), 0.89 (s, 9H), 1.39 (s, 3H), 1.46 (s, 3H), 1.97–2.09 (m, 1H), 2.19–2.30 (m, 1H), 3.88–3.92 (m, 1H), 3.98–4.09 (m, 4H), 4.62–4.68 (m, 1H), 5.76–5.82 (m, 1H)

Preparation of 27B from 27A 1.43 ml (19.6 mmol) of dimethyl sulfide were added dropwise at 0° C. to a solution of 2.9 g (16.2 mmol) of n-bromosuccinimide in 100 ml of anhydrous dichloromethane. After 5 min, the mixture was cooled to −20° C. and 3.4 g (10.8 mmol) of 27A dissolved in 20 ml of anhydrous dichloromethane were added dropwise. The light yellow suspension was then slowly warmed to 25° C. and stirred for 3 h. It was then treated with 100 ml of saturated ammonium chloride solution and extracted using 500 ml of ethyl acetate. The combined organic phases were washed with saturated sodium chloride solution and dried using magnesium sulfate. After concentration, the residue was purified by chromatography on silica gel (eluent: ethyl acetate/heptane 1:3) and 3.7 g (98%) of 27B were obtained as a colorless oil.

¹H-NMR (270 MHz, CDCl₃) δ=0.09 ppm (s, 3H), 0.10 (s, 3H), 0.89 (s, 9H), 1.38 (s, 3H), 1.41 (s, 3H), 2.09–2.21 (m, 1H), 2.35–2.45 (m, 1H), 3.92 (s, 2H), 3.97–4.05 (m, 2H), 4.38–4.65 (m, 1H), 5.83–5.89 (m, 1H)

MS (Cl): 377.1 (M+H+).

Preparation of 27C from 27B 3.0 g (7.6 mmol) of 27B were heated at 90° C. for 6 h in 42 ml of trimethyl phosphite. The excess phosphite was then removed by distillation in vacuo and the residue was purified by chromatography on silica gel (eluent: ethyl acetate/methanol 5:1). 3.0 g (93%) of 27C were obtained as a colorless oil.

Preparation of 27D from 27C 3.0 g (7.4 mmol) of 27C were dissolved in 50 ml of methanol. 1 ml of 1N hydrochloric acid was added. After 24 h, the reaction solution was neutralized using 1N sodium hydroxide solution and concentrated to dryness in vacuo. The residue was taken up in 50 ml of anhydrous dichloromethane, 5 ml of dimethoxypropane and 0.5 g of pyridinium p-toluenesulfonate were added and the mixture was heated at 40° C. for 4 h. The solution was then added to saturated sodium hydrogencarbonate solution and the mixture was extracted using 500 ml of ethyl acetate. The combined organic phases were washed with saturated sodium chloride solution, dried using magnesium sulfate and concentrated in vacuo. The residue was purified by chromatography on silica gel (eluent: ethyl acetate/methanol 10:1) and 1.5 g (70%) of 27D were obtained as a colorless oil.

Preparation of 27 from 27D

The compound 27 was obtained from 27D analogously to the synthesis procedures e-f (as described under 8).

$^1$H-NMR (200 MHz, d$_6$-DMSO): δ=2.05–2.22 ppm (m, 1H), 2.55–2.8 (m, 1H), 3.4–3.55 (m, 1H), 3.6 (s, 3H), 3.65 (s, 3H), 4.05–4.15 (m, 1H), 4.3–4.4 (m, 1H), 4.6–4.8 (m, 3H), 5.0–5.15 (m, 1H), 5.55–5.68 (m, 1H), 6.3–6.45 (m, 1H), 6.37–6.45 (m, 2H), 7.5–7.7 (m, 3H), 10.0 (s, 1H).

MS (Cl): 399 (M+), 381 (M+-H$_2$O).

Preparation of 28 from 27

135 mg (0.34 mmol) of 27 were dissolved in 10 ml of anhydrous acetonitrile. 155 mg (1 mmol) of trimethylsilyl bromide were added dropwise at 0° C. The mixture was stirred for 30 minutes and 5 ml of water were then added. It was treated with 1N sodium hydroxide solution until a pH of about 5 was obtained and concentrated in vacuo. The residue was purified by chromatography on RP-8 silica gel (eluent: water/methanol 4:1) and 23 mg (18%) of 28 were obtained as a colorless solid. M.p.: 180°–185° C.

The pharmaceutical preparations are prepared according to generally customary processes.

EXAMPLE 1 Tablets

Tablets which are suitable for oral administration and which contain the below-mentioned constituents were prepared in a manner known per se by granulating active compounds and auxiliaries and then pressing to give tablets.

| Constituents (per tablet) | Weight (mg) |
| --- | --- |
| Compound of the formula I (e.g. compound 17) | 50 mg |
| Lactose | 100 mg |
| Cornstarch | 30 mg |
| Talc | 3 mg |
| Colloidal silica | 3 mg |

-continued

| Constituents (per tablet) | Weight (mg) |
| --- | --- |
| Magnesium stearate | 2 mg |

EXAMPLE 2 Capsules

Capsules which are suitable for oral administration contained the below-mentioned constituents and were prepared in a manner known per se by mixing active compounds and auxiliaries and filling into gelatin capsules.

| Constituents (per tablet) | Weight (mg) |
| --- | --- |
| Compound of the formula I (e.g. compound 21) | 50 mg |
| Lactose | 100 mg |
| Cornstarch | 30 mg |
| Talc | 3 mg |
| Colloidal silica | 3 mg |
| Magnesium stearate | 2 mg |

We claim:
1. A cyclohexane derivative of the formula I

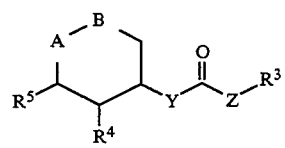

in which
A—B is the group

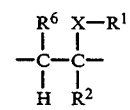

or
the group

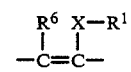

$R^1$ is: CN, COOH, COO—(C$_1$-C$_4$-alkyl), C$_1$-C$_4$-alkanoyl, SO$_3$—(C$_1$-C$_4$-alkyl), SO$_3$H, PO(OH)$_2$, PO(OH)(O—C$_1$-C$_4$-alkyl) or PO(O—C$_1$-C$_4$-alkyl)$_2$, $R^2$ is: H, OH or F, $R^3$ is: H, phenyl, naphthyl, pyridyl, thienyl or furyl, where the aromatic or heteroaromatic system can be monosubstituted or polysubstituted by F, Cl, Br, I, OH, NO$_2$, C$_1$-C$_4$-alkanoyl, C$_1$-C$_4$-alkoxy, C$_1$-C$_4$-alkyl, phenyl, phenoxy, thienyl, furyl, pyridyl, imidazolyl or benzyloxy, where the substituents are identical or different, $R^4$, $R^5$ and $R^6$ are: H, OH, F, Cl, Br, C$_1$-C$_4$-alkanoyl, C$_1$-C$_4$-alkyl, phenyl, phenoxy, thienyl, furyl, pyridyl, imidazolyl or benzyloxy, where $R^4$, $R^5$ and $R^6$ are identical or different, X is: —(CH$_2$)$_n$—, —CH=CH— or —CH$_2$OCH$_2$—, Y is: —(CH$_2$)$_n$—, O, S or NH, Z is: —(CH$_2$)$_n$— or —CH=CH— and n is: zero, 1, 2, 3 or 4 for inhibition of the glucose-6-phosphatase system of the liver in mammals.

2. A compound as claimed in claim 1, in which the radicals in formula I have the following meaning:

$R^1$ is: COOH, COO—($C_1$-$C_4$-alkyl), PO(OH)$_2$PO(OH)(O—$C_1$-$C_4$-alkyl) or PO(O—$C_1$-$C_4$-alkyl)$_2$, $R^2$ is: H or OH, $R^3$ is: H, phenyl, naphthyl, pyridyl, thienyl or furyl, where the aromatic or heteroaromatic system can be monosubstituted, disubstituted or trisubstituted by F, Cl, Br, I, NO$_2$, OH, $C_1$-$C_4$-alkanoyl, $C_1$-$C_4$-alkoxy, $C_1$-$C_4$-alkyl, phenyl, phenoxy, thienyl, furyl, pyridyl, imidazolyl or benzyloxy, where the substituents are identical or different, $R^4$, $R^5$ and $R^6$ are: H, OH, F, Cl, Br, $C_1$-$C_4$-alkanoyl, $C_1$-$C_4$-alkyl, phenyl, phenoxy, thienyl, furyl, pyridyl, imidazolyl or benzyloxy, where $R^4$, $R^5$ and $R^6$ are identical or different, X is: —(CH$_2$)$_n$—, —CH=CH— or —CH$_2$OCH$_2$—, Y is: —(CH$_2$)$_n$—, O, S or NH, Z is: —(CH$_2$)$_n$—or —CH=CH— and n is: zero, 1, 2, 3 or 4 for inhibition of the glucose-6-phosphatase system in mammals.

3. A compound of the formula I as claimed in claim 1, in which the radicals have the following meaning:

$R^1$ is: COOH or COO—($C_1$-$C_4$-alkyl), $R^2$ is: H or OH, $R^3$ is: H, phenyl, naphthyl, pyridyl, thienyl or furyl, where the aromatic or heteroaromatic system can be monosubstituted, disubstituted or trisubstituted by identical or different F, Cl, OH, NO$_2$, $C_1$-$C_4$-alkanoyl, $C_1$-$C_4$-alkoxy, $C_1$-$C_4$-alkyl, phenyl, phenoxy or benzyloxy, $R^4$, $R^5$ and $R^6$ are: H or OH, where $R^4$, $R^5$ and $R^6$ are identical or different, X is: —(CH$_2$)$_n$— and n=zero, 1 or 2, Y is: O or NH, Z is: —(CH$_2$)$_n$—, where n=0 or 2, or —CH=CH— for inhibition of the glucose-6-phosphatase system in mammals.

4. A method for the treatment of disorders which are characterized by an increased glucose discharge from the liver or an increased activity of the glucose-6-phosphatase system which comprises administering to a host in need of such treatment an effective amount of a compound of the formula I as claimed in claim 1.

5. A method as claimed in claim 4 for the treatment of diseases which are associated with an increased activity of the glucose-6-phosphatase system.

6. A method as claimed in claim 4 for the treatment of diseases which are associated with an increased glucose production of the liver.

7. A method as claimed in claim 4 for the treatment of type II diabetes.

8. A method for the production of pharmaceuticals for the treatment of disorders which are characterized by an increased glucose discharge from the liver or an increased activity of the glucose-6-phosphatase system which comprises incorporating in said pharmaceuticals an effective amount of a compound of the formula I as claimed in claim 1.

9. A method as claimed in claim 8 for the production of pharmaceuticals for the treatment of type II diabetes.

10. A pharmaceutical composition for the treatment of disorders which are characterized by an increased glucose discharge from the liver or an increased activity of the glucose-6-phosphatase system, containing an effective amount for said treatment of a compound of the formula I as claimed in claim 1 together with a pharmaceutically acceptable diluent or excipient.

11. A pharmaceutical composition as claimed in claim 10 for the treatment of type II diabetes.

12. A method for the treatment of disorders which are characterized by an increased glucose discharge from the liver or an increased activity of the glucose-6-phosphatase system which comprises administering to a host in need of such treatment a pharmaceutical composition as claimed in claim 10.

13. A method as claimed in claim 12 for the treatment of type II diabetes.

* * * * *

UNITED STATES PATENT AND TRADEMARK OFFICE
CERTIFICATE OF CORRECTION

PATENT NO. : 5,451,573
DATED : September 19, 1995
INVENTOR(S) : Horst HEMMERLE et al It is certified that error appears in the above-indentified patent and that said Letters Patent is hereby corrected as shown below:

Claim 2, Column 31, Line 3, after "PO(OH)$_2$" insert --,--.

Signed and Sealed this

Nineteenth Day of November, 1996

Attest:

BRUCE LEHMAN

Attesting Officer     Commissioner of Patents and Trademarks